United States Patent
Itzhaky et al.

(10) Patent No.: US 6,767,717 B1
(45) Date of Patent: Jul. 27, 2004

(54) METHOD AND KIT FOR THE DETECTION OF EXPLOSIVES

(76) Inventors: Harel Itzhaky, 27 Mordechi Street, Kiriyat Tivon (IL), 36023; Ehud Keinan, Moran Street 8, Timrat (IL), 10505

(*) Notice: Subject to any disclaimer, the term of this patent is extended or adjusted under 35 U.S.C. 154(b) by 0 days.

(21) Appl. No.: 09/914,268

(22) PCT Filed: Feb. 24, 1999

(86) PCT No.: PCT/IL99/00112

§ 371 (c)(1), (2), (4) Date: Feb. 15, 2002

(87) PCT Pub. No.: WO99/43846

PCT Pub. Date: Sep. 2, 1999

(30) Foreign Application Priority Data

Feb. 25, 1998 (IL) .................................................. 123451

(51) Int. Cl.[7] .......................... C12Q 1/28; G01N 33/22
(52) U.S. Cl. ......................... 435/28; 435/192; 435/810; 436/135; 436/128
(58) Field of Search ......................... 435/28, 192, 810; 436/135, 128

(56) References Cited

U.S. PATENT DOCUMENTS 5,006,461 A * 4/1991 Woiszwillo ................ 435/7.92
5,736,353 A * 4/1998 Weavers et al. ............... 435/28

FOREIGN PATENT DOCUMENTS

| GB | 1177516 | 1/1970 |
|---|---|---|
| GB | 2314156 | 12/1997 |
| WO | WO 79/00122 | 3/1979 |

OTHER PUBLICATIONS

Database Chemabs Chemical Abstracts Service, Columbus Ohio, Abstract of: Claudia Keuchel et al., "Enzyme–linked immunosorbent assay for the determination of 2, 4, 6–trinitroluene and related nitroaromatic compounds", *Anal. Science*, 1992, pp. 9–12, 8(1).

Database Chemabs Chemical Abstracts Service, Columbus Ohio, Abstract of: Tudor Fernando et al., "Biological Decontamination of Water Contaminated with Explosives by Phanerochaete Chrysosporium", *Gas, Oil, Coal, Environ. Biotechnol. 3*, [Pap. IGT's Symp.] 3rd, 1991, meeting date 1990, pp. 193–206.

* cited by examiner

*Primary Examiner*—Francisco Prats
(74) *Attorney, Agent, or Firm*—Browdy and Neimark, P.L.L.C.

(57) ABSTRACT

The present invention provides a method of detecting a peroxide-based explosive in a sample suspected of consisting of or comprising such explosive, which method comprises dissolving said sample in a suitable organic solvent, contacting the solution with an aqueous solution of a strong acid capable of decomposing said explosive to release hydrogen peroxide, and contacting the resulting mixture with a peroxidase enzyme. The invention also provides a kit for use in the method of the invention.

20 Claims, No Drawings

METHOD AND KIT FOR THE DETECTION OF EXPLOSIVES

REFERENCE TO RELATED APPLICATIONS

The present application is the national stage under 35 U.S.C. 371 of international application PCT/IL99/00112, filed Feb. 24, 1999 which designated the United States, and which international application was published under PCT Article 21(2) in the English language.

FIELD OF THE INVENTION

This invention concerns a method of detecting peroxide-based explosives and a kit for use in this method.

Improvised explosive devices based on peroxide containing materials have increasingly been used in recent years by various terrorist organizations, especially in Israel, as well as in the UK and the USA. The main reason is that such peroxide-based explosives can be easily "home-made" using inexpensive, readily available starting materials which can be purchased in most hardware and paint stores, even in bulk quantities. One class of such peroxide-based explosives can be easily produced by reacting various carbonyl compounds (e.g. ketones, aldehydes and their derivatives) with hydrogen peroxide under acid catalysis. For example, when a mixture of acetone, hydrogen peroxide and small amounts of a mineral acid, e.g. sulfuric acid, is left for several hours at room temperature, white crystals of triacetone triperoxide (hereinafter "TATP") and diacetone diperoxide (hereinafter "DADP") are formed by the following reaction:

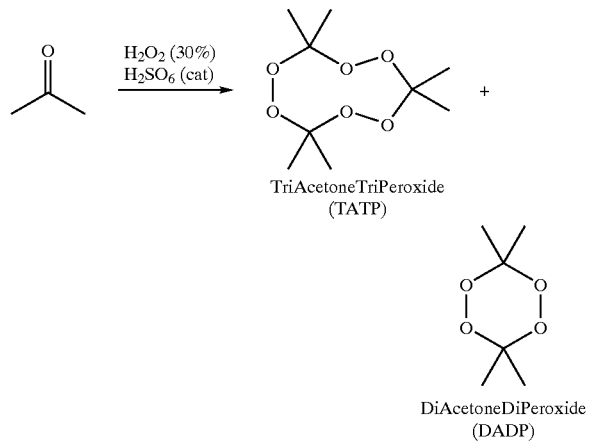

These crystals are collected and can be stashed with water or with 10% sodium carbonate solution. TATP and DADP are powerful initiators by themselves and can be used as the main filler in home-made detonators. They are quite unstable explosives and may explode under rough handling, scratching with metals or by sparks and open flame, even when they contain up to 25% water or even when immersed in water. The explosive intensity of TATP is approximately ⅝ that of TNT. This material is quite volatile, unless used shortly after its manufacture, should be stored in a cool, dark dry place. It has been reported that at room temperature TATP loses ⅔ of its weight within 14 days and at 50° C. it evaporates completely within 40 days.

Another commonly used peroxide based explosive is hexamethylenetriperoxidediamine (hereinafter "HMTD"). It can be conveniently prepared by treating hexamethylenetetramine with hydrogen peroxide in the presence of a weak acid, such as citric acid, in order to neutralize the liberated ammonia. The reaction can be represented as follows:

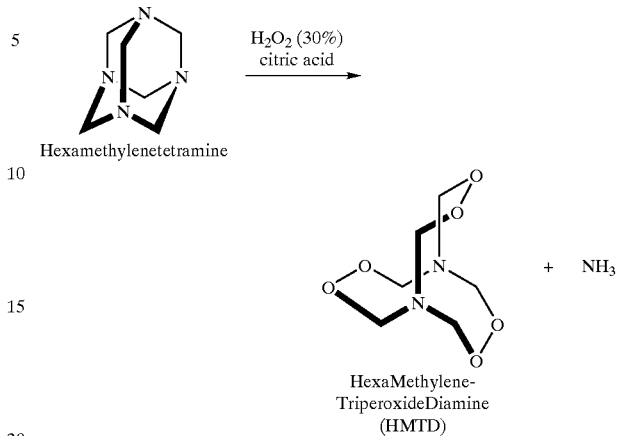

HMTD is almost insoluble in water and in common organic solvents at room temperature. It is too active and too unstable to be of commercial use as an explosive.

Although many peroxide containing materials of the above-described type are known for more than 70 years, no satisfactory method for their detection has been suggested to date. The detection of peroxide-based explosives is particularly difficult because all these materials do not contain nitro groups or any other nitrogen oxide functional groups. Since most of the currently available explosive detectors are based on the detection of nitro groups, they cannot be employed for detection of peroxide-based materials. Consequently, and in view of the increased use of such peroxide-based explosives by terrorists, especially in the Middle East as well as in other parts of the world, there exists an urgent need for highly sensitive method, and devices for the early detection of peroxide-based explosives and improvised explosive devices employing them.

OBJECT OF THE INVENTION

It is thus the object of the present invention to provide a reliable method for the fast and easy detection of peroxide-based explosives.

It is a further object of the invention to provide a portable kit for the simple yet reliable and selective detection and identification of peroxide based explosives.

SUMMARY OF THE INVENTION

The above object was achieved by the present invention which provides a method of detecting a peroxide-based explosive in a sample suspected of consisting of or comprising such explosive, which method comprises dissolving said sample in a suitable organic solvent, contacting the solution with an aqueous solution of a strong acid capable of decomposing said explosive to release hydrogen peroxide, and contacting the resulting mixture with a peroxidase enzyme, a buffer to adjust the pH to such permitting action of the peroxidase enzyme and a substrate capable of being oxidized by the oxidant under the catalysis of the peroxidase enzyme to produce a pronounced change in a measurable physical parameter of the substrate.

The invention also provides, in a second aspect thereof, a kit for use in a method of the invention, comprising packaged organic solvent, packaged aqueous solution of a strong acid, packaged buffer, packaged peroxidase enzyme and packaged substrate.

DETAILED DESCRIPTION OF THE INVENTION

In accordance with the method of the present invention, a sample to be tested for the presence of peroxide-based explosive, is dissolved in a suitable organic solvent and contacted with a strong acid in the presence of water, whereby any peroxide-containing material is decomposed to release free hydrogen peroxide. The resulting mixture is neutralized with a suitable buffer and the presence of peroxide in the mixture is detected by means of a peroxidase enzyme and a substrate which is oxidized with a resulting pronounced change in a measurable physical parameter thereof. When a such a change is observed the result of the test is a positive indication of the presence of peroxide-based explosive in the tested sample.

The peroxide enzyme serves as a catalyst in the above process, so that only a small amount of the enzyme is needed for the oxidation of comparatively large amounts of the substrate. Any readily available peroxidase enzyme can be used, for example Horseradish peroxidase or soy bean peroxidase. A preferred peroxidase enzyme is the Horseradish peroxidase which is highly selective for hydrogen peroxide.

The invention also contemplates the use of a peroxidase enzyme which is immobilized on a solid support for example on a probe which can be introduced into the test mixture or on the inner surface of a small receptacle wherein the test mixture can be introduced.

The term "substrate" is used, within the context of the present invention, to refer to a compound capable of being oxidized by hydrogen peroxide in the presence of a peroxidase enzyme to yield a product exhibiting a pronounced change in at least one measurable physical parameter as compared to the unoxidized compound. In accordance with a preferred embodiment of the invention this measurable physical parameter is the colour or colour intensity.

Examples of organic solvents suitable for use in the method of the present invention are, for example, tetrahydrofuran, 1,4-dioxane, lower alkanols, dimethysulfoxide, N,N-dimethylforamide, carboxylic acids and sulfonic acids, especially acetic acid and trifluoroacetic acid. Preferred solvents are tetrahydrofuran, 1,4-dioxane and acetic acid.

Strong acids which can be used in the method of the present invention are, for example $H_2SO_4$, HCl, HBr, $HClO_4$, $H_3PO_2$, $H_3PO_3$, $H_3PO_4$ and $HNO_3$. A preferred acid is sulfuric acid which can be used in concentrations of from about 5% to 95%, preferably from about 10% to about 50% by volume in water.

In accordance with an embodiment of the invention the sample to be tested can be introduced into a mixture of the organic solvent and the aqueous solution of the strong acid.

In order to enable the enzymatic reaction of the peroxidase enzyme with the hydrogen peroxide and the substrate, it is necessary to neutralize the acidic mixture of the organic solvent and the aqueous strong acid containing the sample to be tested, so as to adjust its pH to a value between about 5.0 to about 9.0. This can be achieved by a suitable buffer system which should be added to the mixture before the addition of the peroxidase enzyme or simultaneously therewith. In accordance with one embodiment of the invention the buffer is added to the mixture together with the substrate before the mixture is contacted with the peroxidase enzyme. Yet another preferred procedure comprises adding the buffer, the substrate and the peroxidase enzyme simultaneously.

As suitable buffer systems for use in the method of the invention there may be mentioned citrate/phosphate buffer, acetate buffer, phthalate buffer, citrate buffer, phosphate buffer, imidazole buffer, triethanolamine buffer, tris (hydroxymethyl)aminomethane buffer, bis-tris buffer and bis-tris propane buffer. A preferred buffer system is citrate/phosphate buffer 0.1M at pH 5.0.

Thus, in accordance with a preferred embodiment the invention provides a method of detecting a peroxide-based explosive in a sample suspected of consisting of or comprising such explosive, which method comprises introducing said sample into a mixture of an organic solvent and an aqueous solution of a strong acid capable of decomposing said explosive to release hydrogen peroxide, and contacting the resulting mixture with a solution comprising a peroxidase enzyme, a buffer to adjust the pH to such permitting action of the peroxide enzyme and a substrate capable of being oxidized by oxidant under the catalysis of the peroxidase enzyme to produce a pronounced change in the colour of the substrate or its colour intensity.

In this embodiment, the organic solvent is preferably acetic acid and the strong acid is preferably aqueous sulfuric acid 50% by volume. The preferred peroxidase enzyme is Horseradish peroxidase.

In accordance with a further aspect thereof, the invention provides a kit for the detection of a peroxide-based explosive in a sample suspected of consisting of or comprising such explosive, which kit comprises packaged organic solvent, packaged aqueous solution of a strong acid, packaged buffer solution, packaged peroxidase enzyme and packaged substrate.

In a preferred kit according to the invention a mixture of the organic solvent and the aqueous solution of the strong acid are packaged together in the same container. In accordance with another modification of the kit according to the invention the buffer and the substrate are packaged together in the same container.

In accordance with a more preferred embodiment of the kit according to the invention the buffer, the peroxidase enzyme and the substrate are all packaged together. Conveniently the kit according to the invention comprises a plurality of sealed ampoules each containing the peroxidase enzyme, optionally in admixture with the buffer and the substrate, in an amount sufficient for carrying out one test.

The kit according to the present invention may also include a plurality of small reaction vessels, for example small dishes or open receptacles, for carrying out the test therein.

The invention will now be described in more detail in the following non-limit examples.

EXAMPLE 1

A few crystals of TATP (about 1–2 mg) were placed in a shallow well, 0.1 ml of 1,4-dioxane 0.1 ml was added and than 0.1 ml of sulfuric acid 50% v/v in water. The reaction mixture was allowed to stand for 30 seconds before the substrate 2,2'-azino-bis(3-ethylbenzthiazoline-6-sulfonic acid)diammonium salt in 0.2 ml of citrate/phosphate buffer (0.1M at pH 5.0) was added, followed by 0.05 ml of Horseradish peroxidase 5 mg/ml in citrate/phosphate buffer (0.1M at pH 5.0 ml.). An intense bluish-green colour developed in less than 3.0 seconds.

EXAMPLE 2

The procedure of Example 1 was repeated using 1,4-dioxane as solvent instead of the tetrahydrofuran. The same result was obtained.

EXAMPLE 3

The procedure of Example 1 was repeated using 2,7-diaminofluorine as the substrate. A blue-green colour developed in less than 30 seconds.

EXAMPLE 4

The procedure of Example 1 was repeated using 3,3',5,5'-tetramethylbenzidine dihydrochloride as the substrate. An immediate blue colour formation was observed.

EXAMPLE 5

The procedure of Example 1 was repeated using 5-aminosalicylic acid as the substrate A brown colour developed rapidly.

EXAMPLE 6

The procedure of Example 1 was repeated using o-phenylenediamine dihydrochloride as the substrate. An orange colour developed in less than 30 seconds.

EXAMPLE 7

A few crystals of TATP (about 1–2 mg) were placed in a shallow well, 0.1 ml of a 1:1 mixture of sulfuric acid 50% v/v in water and acetic acid was added and the reaction mixture was allowed to stand for 30 seconds before 0.2 ml of a 4:1 mixture of the substrate 2,2'-azinobis(3-ethylbenzthiazoline-6-sulfonic acid)diammonium salt and the enzyme Horseradish peroxidase 5 mg/ml in citrate/phosphate buffer (0.1 M at pH 5.0) was added. An intense bluish-green colour developed in less than 30 seconds.

EXAMPLE 8

The procedure of Example (7) was repeated using the substrates of Examples 3–6. The same results as in these examples were observed.

What is claimed is:

1. A method of detecting peroxide-based explosive in a sample suspected of comprising such explosive, which method comprises dissolving said sample in a suitable organic solvent, contacting the solution with an aqueous solution of a strong acid capable of decomposing said explosive to release hydrogen peroxide, and contacting the resulting mixture with a peroxidase enzyme, a buffer to adjust the pH to such permitting action of the peroxidase enzyme and a substrate capable of being oxidized by the oxidant under the catalysis of the peroxidase enzyme to produce a pronounced change in a measurable physical parameter of the substrate.

2. A method according to claim 1, wherein said physical parameter of the substrate is its colour or colour intensity.

3. A method according to claim 1 or 2, wherein the solvent is selected from the group consisting of lower alkanols, dimethysulfoxide, N,N-dimethylforamide, carboxylic acids, especially acetic acid and trifluoroacetic acid, and sulfonic acids.

4. A method according to claim 3, wherein the organic solvent is acetic acid.

5. A method according to claim 1, wherein the strong acid is selected from the group consisting of $H_2SO_4$, HCl, HBr, $HClO_4$, $H_3PO_2$, $H_3PO_3$, $H_3PO_4$ and $HNO_3$.

6. A method according to claim 5, wherein the strong acid is $H_2SO_4$.

7. A method according to claim 6, wherein the concentration of the aqueous $H_2SO_4$ solution is from about 5% to 95%.

8. A method according to claim 1, wherein the pH is adjusted by said buffer to about 5.0 to about 9.0.

9. A method according to claim 8, wherein the buffer is about 0.01 to 0.5 M citrate/phosphate buffer.

10. A method according to claim 1, wherein the peroxidase enzyme is Horseradish peroxidase.

11. A method according to claim 2, wherein the substrate is selected from the group consisting of 2,2'-azino-bis(3-ethylbenzthiazoline-6-sulfonic acid)diammonium salt, 2,7-diaminofluorene, 3,3',5,5'-tetramethylbenzidine and its dihydrochloride salt, 5-aminosalicylic acid, o-phenylenediamine and its dihydrochloride salt, 5-amino-2,3-dihydro-1,4-phthalazinedione, 3-amino-9-ethylcarbazole, 4-chloro-1-naphthol, 3,3'-diaminobenzidine, o-dianisidine and its dihydrochloride salt, guaiacol and pyrogallol.

12. A method according to claim 1, wherein the sample is introduced into a mixture of the organic solvent and the aqueous solution of the strong acid.

13. A method according to claim 1, wherein the peroxidase enzyme is combined with the buffer prior to being contacted with said resulting mixture.

14. A method according to claim 1, wherein the buffer is combined with the substrate prior to being contacted with said resulting mixture.

15. A method according to claim 1, wherein said resulting mixture is contacted with a combination of the buffer, the peroxidase enzyme and the substrate.

16. A method of detecting peroxide-based explosive in a sample suspected of comprising such explosive, which method comprises introducing said sample into a mixture of an organic solvent and an aqueous solution of a strong acid capable of decomposing said explosive to release hydrogen peroxide, and contacting the resulting mixture with a solution comprising a peroxidase enzyme, a buffer to adjust the pH to such permitting action of the peroxidase enzyme and a substrate capable of being oxidized by the oxidant under the catalysis of the peroxidase enzyme to produce a pronounced change in the colour of the substrate or its colour intensity.

17. A method according to claim 16, wherein the organic solvent is acetic acid.

18. A method according to claim 16 or 17, wherein the strong acid is aqueous sulfuric acid.

19. A method according to claim 16, wherein the peroxidase enzyme is Horseradish peroxidase.

20. A method according to claim 7, wherein said concentration of aqueous $H_2SO_4$ solution is about 10% to about 50% by volume.

* * * * *